United States Patent
Nelson et al.

(10) Patent No.: US 7,052,839 B2
(45) Date of Patent: *May 30, 2006

(54) TERMINAL-PHOSPHATE-LABELED NUCLEOTIDES AND METHODS OF USE

(75) Inventors: John Nelson, Neshanic Station, NJ (US); Carl Fuller, Berkeley Heights, NJ (US); Anup Sood, Flemington, NJ (US); Shiv Kumar, Belle Mead, NJ (US)

(73) Assignee: Amersham Biosciences Corp, Piscataway, NJ (US)

(*) Notice: Subject to any disclaimer, the term of this patent is extended or adjusted under 35 U.S.C. 154(b) by 506 days.

This patent is subject to a terminal disclaimer.

(21) Appl. No.: 10/113,030

(22) Filed: Apr. 1, 2002

(65) Prior Publication Data

US 2003/0077610 A1    Apr. 24, 2003

Related U.S. Application Data

(60) Provisional application No. 60/315,798, filed on Aug. 29, 2001.

(51) Int. Cl.
    *C12Q 1/68* (2006.01)
(52) U.S. Cl. ............................................. 435/6
(58) Field of Classification Search ............. 435/6, 435/7, 91.2, 7.1; 436/501
    See application file for complete search history.

(56) References Cited

U.S. PATENT DOCUMENTS

| | | | |
|---|---|---|---|
| 5,728,525 A * | 3/1998 | Conrad | 435/6 |
| 5,849,487 A | 12/1998 | Hase et al. | |
| 6,187,286 B1 | 2/2001 | Elmaleh et al. | |
| 2003/0064366 A1 * | 4/2003 | Hardin et al. | 435/6 |

FOREIGN PATENT DOCUMENTS

| | | |
|---|---|---|
| WO | WO 96/22297 | 7/1996 |
| WO | WO 99/16832 | 4/1999 |
| WO | WO 02/40126 | 5/2002 |
| WO | WO 03/020734 | 3/2003 |
| WO | WO 03/020891 | 3/2003 |

OTHER PUBLICATIONS

Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.
Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB, vol. 6, No. 22, Nov. 19, 1996, pp. 2639-2642.
Su, S-H., et al. "Novel non-nucleosidic phosphoramidites for oligonucleotide modification and labeling" Bioorganic and Medicinal Chemistry Letters, Oxford, GB, vol. 7, No. 13, Jul. 8, 1997, pp. 1639-1644.
Arzumanov Andrey, A., et al. "Gamma-Phosphate-substituted 2'-deoxynucleoside 5'-triphosphates as substrates for DNA polymerases" Journal of Biological Chemistry, vol. 271, No. 40, 1996, pp. 24389-24394.

* cited by examiner

*Primary Examiner*—Jeffrey Fredman
*Assistant Examiner*—Heather G. Calamita
(74) *Attorney, Agent, or Firm*—Royal N. Ronning, Jr.; Yonggang Ji

(57) ABSTRACT

The present invention describes methods of detecting a nucleic acid in a sample, based on the use of terminal-phosphate-labeled nucleotides as substrates for nucleic acid polymerases. The methods provided by this invention utilize a nucleoside polyphosphate, dideoxynucleoside polyphosphate, or deoxynucleoside polyphosphate analogue which has a colorimetric dye, chemiluminescent, or fluorescent moiety, a mass tag or an electrochemical tag attached to the terminal-phosphate. When a nucleic acid polymerase uses this analogue as a substrate, an enzyme-activatable label would be present on the inorganic polyphosphate by-product of phosphoryl transfer. Cleavage of the polyphosphate product of phosphoryl transfer via phosphatase leads to a detectable change in the label attached thereon. When the polymerase assay is performed in the presence of a phosphatase, there is provided a convenient method for real-time monitoring of DNA or RNA synthesis and detection of a target nucleic acid.

74 Claims, 2 Drawing Sheets

US 7,052,839 B2

TERMINAL-PHOSPHATE-LABELED NUCLEOTIDES AND METHODS OF USE

RELATED APPLICATIONS

This application claims priority benefit under Title 35 §119(e) of U.S. Provisional Application No. 60/315,798 filed Aug. 29, 2001.

FIELD OF THE INVENTION

The present invention relates generally to methods of detecting a polynucleotide in a sample, based on the use of terminal-phosphate-labeled nucleotides including three or more phosphates as substrates for nucleic acid polymerases. The labels employed are enzyme-activatable and include chemiluminescent, fluorescent, electrochemical and chromophoric moieties as well as mass tags.

BACKGROUND OF THE INVENTION

Methods are known for detecting specific nucleic acids or analytes in a sample with high specificity and sensitivity. Such methods generally require first amplifying nucleic acid sequence based on the presence of a specific target sequence or analyte. Following amplification, the amplified sequences are detected and quantified. Conventional detection systems for nucleic acids include detection of fluorescent labels, fluorescent enzyme-linked detection systems, antibody-mediated label detection, and detection of radioactive labels.

One disadvantage of detection methods presently widely in use is the need to separate labeled starting materials from a final labeled product or by-product. Such separations generally require gel electrophoresis or immobilization of a target sequence onto a membrane for detection. Moreover, there are often numerous reagents and/or incubation steps required for detection.

It has been known that DNA and RNA polymerases are able to recognize and utilize nucleosides with a modification at or in place of the gamma position of the triphosphate moiety. It is further known that the ability of various polymerases to recognize and utilize gamma-modified nucleotide triphosphates (NTP's) appears to vary depending on the moiety attached to the gamma phosphate. In general, RNA polymerases are more promiscuous than DNA polymerases.

A colorimetric assay for monitoring RNA synthesis from RNA polymerases in presence of a gamma-phosphate modified nucleotide has been previously reported. In this prior report, RNA polymerase reactions were performed in the presence of a gamma-modified, alkaline phosphatase resistant nucleotide triphosphate which was modified at its gamma-phosphate with a dinitrophenyl group. When RNA polymerase reactions were performed in the presence of this gamma-modified NTP as the sole nucleotide triphosphate and a homopolymeric template, it was found that RNA polymerase could recognize and utilize the modified NTP. Moreover, when the polymerase reactions were performed in the presence of an alkaline phosphatase, which digested the p-nitrophenyl pyrophosphate aldo-product of phosphoryl transfer to the chromogenic p-nitrophenylate, an increase in absorbence was reported. A disadvantage of this detection method is that the real-time colorimetric assay, performed in the presence of an alkaline phosphatase, only works with a homopolymeric template.

It would, therefore, be of benefit to provide a method for detecting RNA in the presence of a heteropolymeric template, which method would not be restricted to using a single terminal-phosphate modified nucleotide as the sole nucleotide that is substantially non-reactive to alkaline phosphatase. This would allow for a single-tube assay for real-time monitoring of RNA synthesis using hetero-polymeric templates.

It would further be of benefit to provide for similar assays for RNA wherein the identity of the label on the terminal-phosphate is varied to allow for better recognition and utilization by RNA polymerase. Furthermore, it is desired that the label on the terminal-phosphate could be varied so as to allow for chemiluminescent and fluorescent detection, analysis by mass or reduction potential, as well as for improved colorimetric detection, wherein only simple and routine instrumentation would be required for detection.

Given that DNA polymerases are known in the art to be less promiscuous than RNA polymerases regarding recognition and utilization of terminally-modified nucleotides, wherein the identity of the moiety at the terminal position can largely affect the DNA polymerase's specificity toward the nucleotide, it would be highly desired to provide for a non-radioactive method for detecting DNA by monitoring DNA polymerase activity. Furthermore, it would be desired that the synthesis and detection of DNA could be accomplished in a single-tube assay for real-time monitoring and that the label at the terminal-phosphate of nucleotide substrates could encompass chemiluminescent, fluorescent, and colorimetric detection, as well as analysis by mass or reduction potential.

SUMMARY OF THE INVENTION

The present invention provides for a method of detecting the presence of a nucleic acid sequence including the steps of: a) conducting a nucleic acid polymerase reaction, wherein the reaction includes the reaction of at least one nucleotide which is substantially non-reactive to phosphatase and at least one terminal-phosphate-labeled nucleotide, which reaction results in the production of labeled polyphosphate; b) permitting the labeled polyphosphate to react with a phosphatase to produce a detectable species; and c) detecting the presence of the detectable species. A definition of phosphatase in the current invention includes any enzyme which cleaves phosphate mono esters, polyphosphates and nucleotides to release inorganic phosphate. In the context of the present invention, this enzyme does not cleave a terminally labeled nucleoside phosphate (i.e. the terminal-phosphate-labeled nucleotide is substantially non-reactive to phosphatase). The phosphatase definition herein provided specifically includes, but is not limited to, alkaline phosphatase (EC 3.1.3.1) and acid phosphatase (EC 3.1.3.2). The definition of a nucleotide in the current invention includes a natural or modified nucleoside phosphate.

The invention further provides for a method of detecting the presence of a DNA sequence including the steps of: a) conducting a DNA polymerase reaction in the presence of a terminal-phosphate-labeled nucleotide, which reaction results in the production of a labeled polyphosphate; b) permitting the labeled polyphosphate to react with a phosphatase to produce a detectable species; and c) detecting the presence of the detectable species.

Also provided is a method of detecting the presence of a nucleic acid sequence comprising the steps of: (a) conducting a nucleic acid polymerase reaction in the presence of at least one terminal-phosphate-labeled nucleotide having four or more phosphate groups in the polyphosphate chain, which reaction results in the production of a labeled polyphosphate; and (b) detecting the labeled polyphosphate.

In addition, the invention relates to a method of detecting the presence of a nucleic acid sequence comprising the steps of: (a) conducting a nucleic acid polymerase reaction in the presence of at least one terminal-phosphate-labeled nucleotide having four or more phosphate groups in the polyphosphate chain, which reaction results in the production of a labeled polyphosphate; (b) permitting the labeled polyphosphate to react with a phosphatase to produce a detectable species; and (c) detecting the presence of the detectable species.

A further aspect of the present invention relates to a method of quantifying a nucleic acid including the steps of: (a) conducting a nucleic acid polymerase reaction, wherein the reaction includes the reaction of a nucleotide which is substantially non-reactive to phosphatase and at least one terminal-phosphate-labeled nucleotide, which reaction results in production of labeled polyphosphate; (b) permitting the labeled polyphosphate to react with a phosphatase to produce a detectable by-product species in an amount substantially proportional to the amount of nucleic acid; (c) measuring the detectable species; and (d) comparing the measurements using known standards to determine the quantity of nucleic acid.

The invention further relates to a method of quantifying a DNA sequence including the steps of: (a) conducting a DNA polymerase reaction in the presence of a terminal-phosphate-labeled nucleotide, the reaction resulting in production of labeled polyphosphate; (b) permitting the labeled polyphosphate to react with a phosphatase to produce a detectable by-product species in amounts substantially proportional to the amount of the DNA sequence; (c) measuring the detectable species; and (d) comparing the measurements using known standards to determine the quantity of DNA.

Another aspect of the invention relates to a method for determining the identity of a single nucleotide in a nucleic acid sequence, which includes the steps of: (a) conducting a nucleic acid polymerase reaction in the presence of at least one terminal phosphate-labeled nucleotide, which reaction results in the production of labeled polyphosphate; (b) permitting the labeled polyphosphate to react with a phosphatase to produce a detectable species; (c) detecting the presence of the detectable species; and (d) identifying the nucleoside incorporated.

Also provided is a method for determining the identify of a single nucleotide in a nucleic acid sequence including the following steps: (a) conducting a nucleic acid polymeric reaction in the presence of at least one terminal-phosphate-labeled nucleotide having four or more phosphate groups in the polyphosphate chain, which reaction results in the production of labeled polyphosphate; (b) permitting the labeled polyphosphate to react with a phosphatase to produce a detectable species; (c) detecting the presence of said detectable species; and (d) identifying the nucleoside incorporated.

The present invention further includes a nucleic acid detection kit wherein the kit includes:

(a) at least one or more terminal-phosphate-labeled nucleotide according to Formula I below:

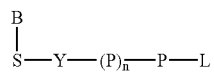

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

(b) at least one of DNA polymerase, RNA polymerase, or reverse transcriptase; and (c) phosphatase.

DETAILED DESCRIPTION OF THE PREFERRED EMBODIMENT

Figure 1:
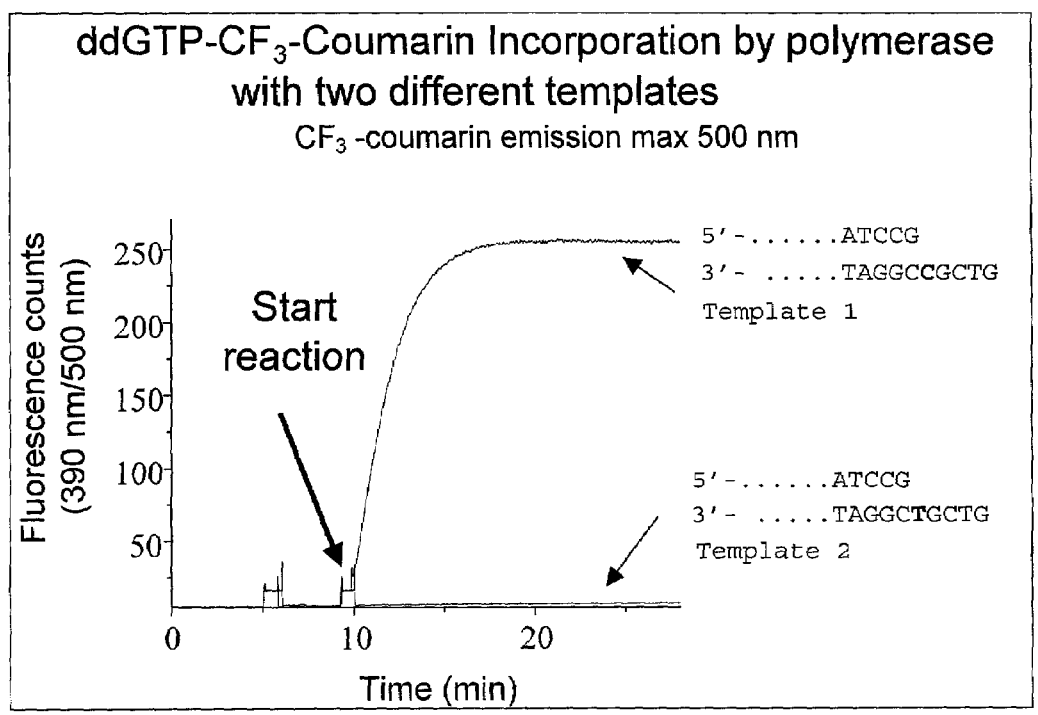
FIG. 1 is a graph showing fluorescence obtained by polymerase utilization of a gamma-phosphate-labeled ddGTP in a template-directed process in the presence of phosphatase.

The term "nucleoside" as defined herein is a compound including a purine deazapurine, pyrimidine or modified base linked to a sugar or a sugar substitute, such as a carbocyclic or acyclic moiety, at the 1' position or equivalent position and includes 2'-deoxy and 2'-hydroxyl, and 2',3'-dideoxy forms as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

The present invention relates to methods of detecting a polynucleotide in a sample wherein a convenient assay is used for monitoring RNA or DNA synthesis via nucleic acid polymerase activity. RNA and DNA polymerases synthesize oligonucleotides via transfer of a nucleoside monophosphate from a nucleoside triphosphate (NTP) or deoxynucleoside triphosphate (dNTP) to the 3' hydroxyl of a growing oligonucleotide chain. The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

In certain embodiments, the polymerase is a DNA polymerase, such as DNA polymerase I, II, or III or DNA polymerase α, β, γ, or terminal deoxynucleotidyl transferase or telomerase. In other embodiments, suitable polymerases include, but are not limited to, a DNA dependent RNA polymerase, a primase, or an RNA dependant DNA polymerase (reverse transcriptase).

The methods provided by this invention utilize a nucleoside polyphosphate, such as a deoxynucleoside polyphosphate, dideoxynucleoside polyphosphate, carbocyclic nucleoside polyphosphate, or acrylic nucleoside polyphosphate analogue with an electrochemical label, mass tag, or a colorimetric dye, chemiluminescent, or fluorescent label attached to the terminal-phosphate. When a nucleic acid polymerase uses this analogue as a substrate, an enzyme-activatable label would be present on the inorganic polyphosphate by-product of phosphoryl transfer. Cleavage of the polyphosphate product of phosphoryl transfer via phosphatase, leads to a detectable change in the label attached thereon. It is noted that while RNA and DNA polymerases are able to recognize nucleotides with modified terminal phosphoryl groups, the inventors have determined that this starting material is not a template for phosphatases. The scheme below shows the most relevant molecules in the methods of this invention; namely the terminal-phosphate-labeled nucleotide, the labeled polyphosphate by-product and the enzyme-activated label.

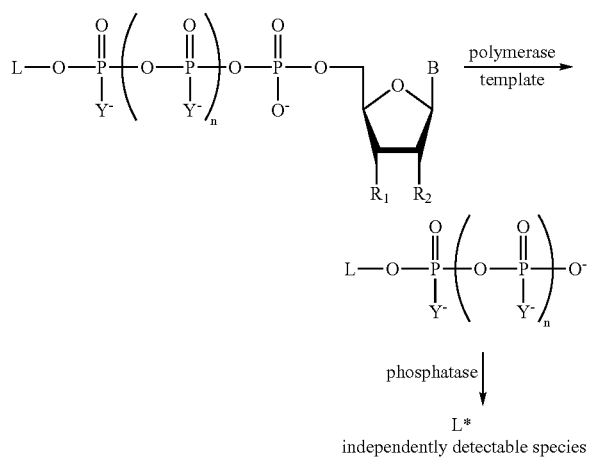

In the scheme above, n is 1 or greater, $R_1$ and $R_2$ are independently H, OH, SH, SR, OR, F, Br, Cl, I, $N_3$, NHR or $NH_2$; B is a nucleotide base or modified heterocyclic base; X is O, S, or NH; Y is O, S, or $BH_3$; and L is a phosphatase activatable label which may be a chromogenic, fluorogenic, chemiluminescent molecule, mass tag or electrochemical tag. A mass tag is a small molecular weight moiety suitable for mass spectrometry that is readily distinguishable from other components due to a difference in mass. An electrochemical tag is an easily oxidizable or reducible species. It has been discovered that when n is 2 or greater, the nucleotides are significantly better substrates for polymerases than when n is 1. Therefore, in preferred embodiments, n is 2, 3 or 4, $R_1$ and $R_2$ are independently H or OH; X and Y are O; B is a nucleotide base and L is a label which may be a chromogenic, fluorogenic or a chemiluminescent molecule.

In one embodiment of the method of detecting the presence of a nucleic acid sequence provided herein, the steps include (a) conducting a nucleic acid polymerase reaction wherein the reaction includes at least one nucleotide which is substantially non-reactive to phosphatase in addition to one terminal-phosphate-labeled nucleotide wherein the polymerase reaction results in the production of labeled polyphosphate; (b) permitting the labeled polyphosphate to react with a phosphatase suitable to hydrolyze the phosphate ester and to produce a detectable species; and c) detecting the presence of a detectable species by suitable means. In this embodiment, the template used for the nucleic acid polymerase reaction may be a heteropolymeric or homopolymeric template. By terminal-phosphate-labeled nucleotide, it is meant throughout the specification that the labeled polyphosphate con-committantly released following incorporation of the nucleoside monophosphate into the growing nucleotide chain, may be reacted with the phosphatase to produce a detectable species. Other nucleotides included in the reaction which are substantially non-reactive to phosphatase may be, for example, blocked at the terminal-phosphate by a moiety which does not lead to the production of a detectable species. The nucleic acid for detection in this particular embodiment may include RNA, a natural or synthetic oligonucleotide, mitochondrial or chromosomal DNA.

The invention further provides a method of detecting the presence of a DNA sequence including the steps of (a) conducting a DNA polymerase reaction in the presence of a terminal-phosphate labeled nucleotide, which reaction results in the production of a labeled polyphosphate; (b) permitting the labeled polyphosphate to react with a phosphatase to produce a detectable species; and (c) detecting the presence of said detectable species. The DNA sequence for detection may include DNA isolated from cells, chemically treated DNA such as bisulfite treated methylated DNA or DNA chemically or enzymatically synthesized according to methods known in the art. Such methods include PCR, and those described in DNA Structure Part A: Synthesis and Physical analysis of DNA, Lilley, D. M. J. and Dahlberg, J. E. (Eds.), Methods Enzymol., 211, Academic Press, Inc., New York (1992), which is herein incorporated by reference. The DNA sequence may further include chromosomal DNA and natural or synthetic oligonucleotides. The DNA may be either double- or single-stranded.

The methods of the invention may further include the step of including one or more additional detection reagents in the polymerase reaction. The additional detection reagent may be capable of a response that is detectably different from the detectable species. For example, the additional detection reagent may be an antibody.

Suitable nucleotides for addition as substrates in the polymerase reaction include nucleoside polyphosphates, such as including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Particularly desired are nucleotides containing 3, 4, or 5 phosphate groups in the polyphosphate chain, where the terminal phosphate is labeled.

It is noted that in embodiments including terminal-phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal-phosphate-labeled nucleotide, the label may be partially quenched by the base. Upon incorporation of the nucleoside monophosphate, the label polyphosphate by-product may be detected due to its enhanced fluorescence. Alternatively, it is possible to physically separate the labeled polyphosphate product by chromatographic separation methods before identification by fluorescence, color, chemiluminescence, or electrochemical detection. In addition, mass spectrometry could be used to detect the products by mass difference.

The methods of the present invention may include conducting the polymerase reaction in the presence of at least one of DNA or RNA polymerase. Suitable nucleic acid polymerases may also include primases, telomerases, terminal deoxynucleotidyl transferases, and reverse transcriptases. A nucleic acid template may be required for the polymerase reaction to take place and may be added to the polymerase reaction solution. It is anticipated that all of the steps (a), (b) and (c) in the detection methods of the present invention could be run concurrently using a single, homogenous reaction mixture, as well as run sequentially It is well within the contemplation of the present invention that nucleic acid polymerase reactions may include amplification methods that utilize polymerases. Examples of such methods include polymerase chain reaction (PCR), rolling circle amplification (RCA), and nucleic acid sequence based amplification (NASBA). For e.g., wherein the target molecule is a nucleic acid polymer such as DNA, it may be detected by PCR incorporation of a gamma-phosphate labeled nucleotide base such as adenine, thymine, cytosine, guanine or other nitrogen heterocyclic bases into the DNA molecule. The polymerase chain reaction (PCR) method is described by Saiki et al in Science Vol. 239, page 487, 1988, Mullis et al in U.S. Pat. No. 4,683,195 and by Sambrook, J. et al. (Eds.), Molecular Cloning, second edition, Cold Spring Harbor Laboratory Press, Cold Spring Harbor, N.Y. (1980), Ausubel, F. M. et al. (Eds.), Current Protocols in Molecular Biology, John Wiley & Sons, Inc., NY (1999), and Wu, R. (Ed.), Recombinant DNA Methodology II, Methods in Zumulogy, Academic Press, Inc., NY, (1995). Using PCR, the target nucleic acid for detection such as DNA is amplified by placing it directly into a reaction vessel containing the PCR reagents and appropriate primers. Typically, a primer is selected which is complimentary in sequence to at least a portion of the target nucleic acid.

It is noted that nucleic acid polymerase reactions suitable for conducting step (a) of the methods of the present invention may further include various RCA methods of amplifying nucleic acid sequences. For example, those disclosed in U.S. Pat. No. 5,854,033 to Lizardi, Paul M., incorporated herein by reference, are useful. Polymerase reactions may further include the nucleic acid sequence based amplification (NASBA) wherein the system involves amplification of RNA, not DNA, and the amplification is iso-thermal, taking place at one temperature (41° C.). Amplification of target RNA by NASBA involves the coordinated activities of three enzymes: reverse transcriptase, Rnase H, and T7 RNA polymerase along with oligonucleotide primers directed toward the sample target RNA. These enzymes catalyze the exponential amplification of a target single-stranded RNA in four steps: extension, degradation, DNA synthesis and cyclic RNA amplification.

Methods of RT-PCR, RCA, and NASBA generally require that the original amount of target nucleic acid is indirectly measured by quantification of the amplification products. Amplification products are typically first separated from starting materials via electrophoresis on an agarose gel to confirm a successful amplification and are then quantified using any of the conventional detection systems for a nucleic acid such as detection of fluorescent labels, enzyme-linked detection systems, antibody-mediated label detection and detection of radioactive labels. In contrast, the present method eliminates the need to separate products of the polymerase reaction from starting materials before being able to detect these products. For example, in the present invention, a reporter molecule (fluorescent, chemiluminescent or a chromophore) or other useful molecule is attached to the nucleotide in such a way that it is undetectable under certain conditions when masked by the phosphate attachment. However, following the incorporation of the nucleotide into the growing oligonucleotide chain and phosphatase treatment of the reaction, the label is detectable under those conditions. For example, if the hydroxyl group on the side of the triple ring structure of 1,3-dichloro-9,9-dimethyl-acridine-2-one (DDAO) is attached to the terminal-phosphate position of the nucleotide, the DDAO does not fluoresce at 659 nm. Once the nucleoside monophosphate is incorporated into DNA, the other product, DDAO polyphosphate (which also does not fluoresce at 659 nm) is a substrate for phosphatase. Once de-phosphorylated to form DDAO, the dye moiety will become fluorescent at 659 nm and hence detectable. The specific analysis of the polyphosphate product can be carried out in the polymerase reaction solution, eliminating the need to separate reaction products from starting materials. This scheme allows for the detection and, optionally, quantitation of nucleic acids formed during polymerase reactions using routine instrumentation such as spectrophotometers.

In the methods described above, the polymerase reaction step may further include conducting the polymerase reaction in the presence of a phosphatase, which converts labeled polyphosphate by-product to the detectable label. As such, a convenient assay is established for detecting the presence of a nucleic acid sequence that allows for continuous monitoring of detectable species formation. This represents a homogeneous assay format in that it can be performed in a single tube.

One format of the assay methods described above may include, but is not limited to, conducting the polymerase reaction in the presence of a single type of terminal-phosphate-labeled nucleotide capable of producing a detectable species, for example terminal-phosphate-modified ATP, wherein all other nucleotides are substantially non-reactive to phosphatase, but yield non-detectable species.

In another assay format, the polymerase reaction may be conducted in the presence of more than one type of terminal-phosphate-labeled nucleotide, each type capable of producing a uniquely detectable species. For example, the assay may include a first nucleotide (e.g., adenosine polyphosphate) that is associated with a first label which when liberated enzymatically from the inorganic polyphosphate by-product of phosphoryl transfer, emits light at a first wavelength and a second nucleotide (e.g., guanosine polyphosphate) associated with a second label that emits light at a second wavelength. Desirably, the first and second wavelength emissions have substantially little or no overlap. It is within the contemplation of the present invention that multiple simultaneous assays based on nucleotide sequence information can thereafter be derived based on the particular label released from the polyphosphate.

In one aspect of the methods of detecting the presence of a nucleic acid sequence described above, the terminal-phosphate-labeled nucleotide may be represented by the following structure (Formula I):

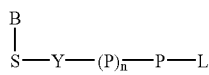

wherein P=phosphate (PO₃) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

For purposes of the methods of the present invention, useful carbocyclic moieties have been described by Ferraro, M. and Gotor, V. in Chem Rev. 2000, volume 100, 4319–48. Suitable sugar moieties are described by Joeng, L. S. et al., in J Med. Chem. 1993, vol. 356, 2627–38; by Kim H. O. et al., in J Med. Chem. 193, vol. 36, 30–7; and by Eschenmosser A., in Science 1999, vol. 284, 2118–2124. Moreover, useful acyclic moieties have been described by Martinez, C. I., et al., in Nucleic Acids Research 1999, vol. 27, 1271–1274; by Martinez, C. I., et al., in Bioorganic & Medicinal Chemistry Letters 1997, vol. 7, 3013–3016; and in U.S. Pat. No. 5,558,91 to Trainer, G. L. Structures for these moieties are shown below, where for all moieties R may be H, OH, NHR, F, N₃, SH, SR, OR lower alkyl and aryl; for the sugar moieties X and Y are independently O, S, or NH; and for the acyclic moieties, X=O, S, NH, NR.

Carbocyclic Moieties

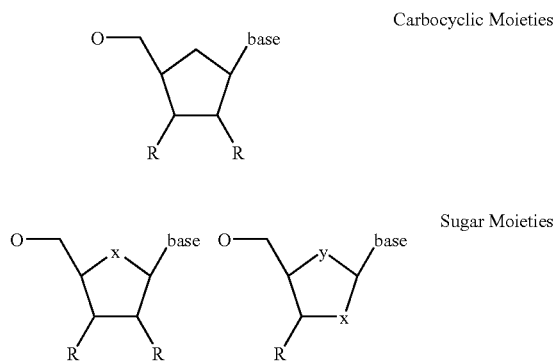

Sugar Moieties

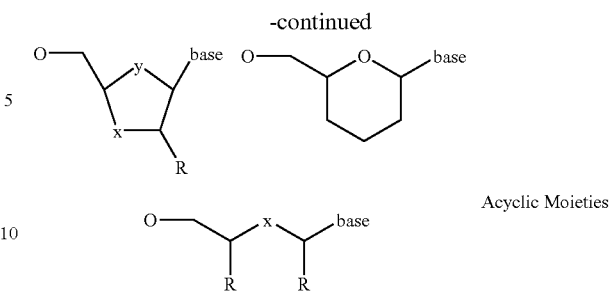

Acyclic Moieties

In certain embodiments, the sugar moiety in Formula I may be selected from the following: ribosyl, 2'-deoxyribosyl, 3'-deoxyribosyl, 2',3'-didehydrodideoxyribosyl, 2',3'-dideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

Moreover, in Formula I, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs therefore.

The label attached at the terminal-phosphate position in the terminal-phosphate-labeled nucleotide may be selected from the group consisting of 1,2-dioxetane chemiluminescent compounds, fluorogenic dyes, chromogenic dyes, mass tags and electrochemical tags. This would allow the detectable species to be detectable by the presence of any one of color, fluorescence emission, chemiluminescene, mass change, electrochemical detection or a combination thereof.

Wherein the phosphorylated label in Formula I is a fluorogenic moiety, it is desirably selected from one of the following (all shown as the phosphomonester): 2-(5'-chloro-2'-phosphoryloxyphenyl)-6-chloro-4-(3H)-quinazolinone, sold under the trade name ELF 97 (Molecular Probes, Inc.), fluorescein diphosphate (tetraammonium salt), fluorescein 3'(6')-O-alkyl-6'(3')-phosphate, 9H-(1,3-dichloro-9,9-dimethylacridin-2-one-7-yl)phosphate (diammonium salt), 4-methylumbelliferyl phosphate (free acid), resorufin phosphate, 4-trifluoromethylumbelliferyl phosphate, umbelliferyl phosphate, 3-cyanoubelliferyl phosphate, 9,9-dimethylacridin-2-one-7-yl phosphate, 6,8-difluoro-4-methylumbelliferyl phosphate and derivatives thereof. Structures of these dyes are shown below:

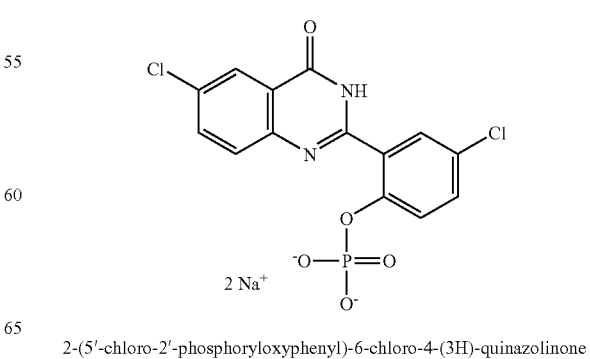

2-(5'-chloro-2'-phosphoryloxyphenyl)-6-chloro-4-(3H)-quinazolinone

-continued

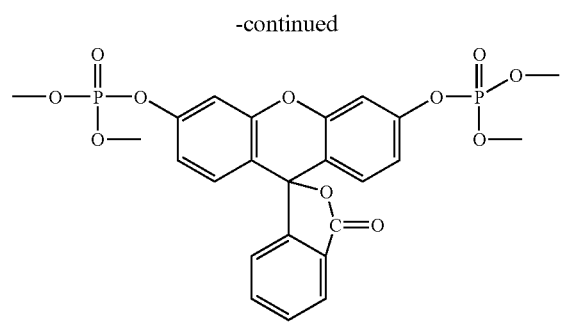

fluorescein diphosphate

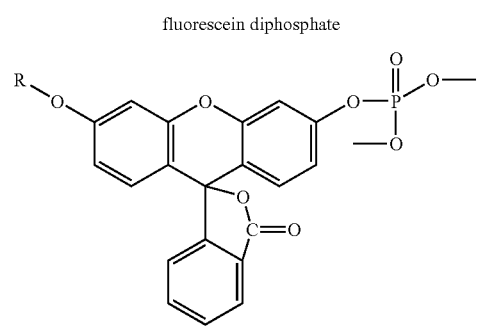

fluorescein 3′(6′)-O-alkyl-6′(3′)-phosphate

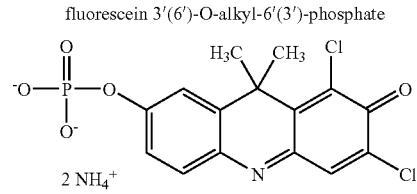

9H-(1,3-dichloro-9,9-dimethylacridin-2-one-7-yl) phosphate(diammonium salt)

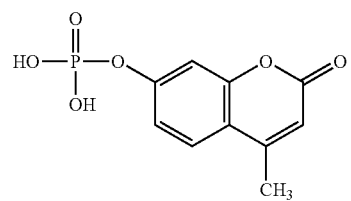

4-methylumbelliferyl phosphate

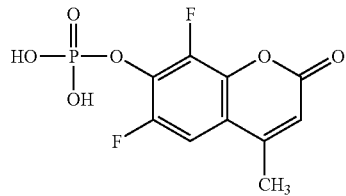

6,8-difluoro-4-methylumbelliferyl phosphate

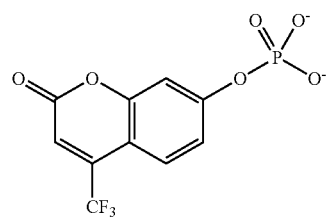

4-Trifluoromethylumbelliferyl phosphate

-continued

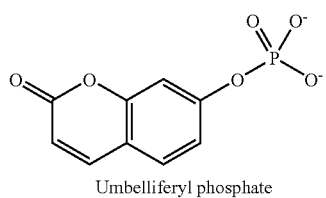

Umbelliferyl phosphate

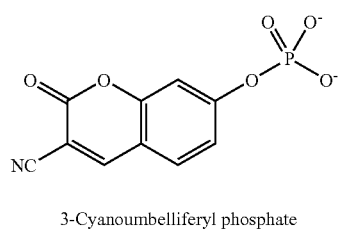

3-Cyanoumbelliferyl phosphate

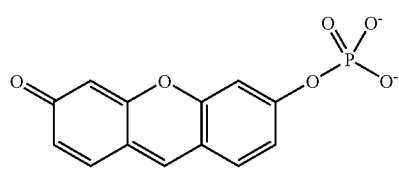

Resorufin phosphate

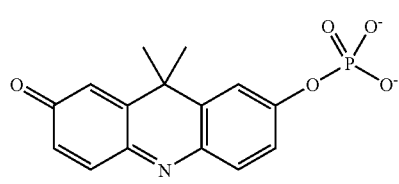

9,9-dimethylacridin-2-one-7-yl phosphate

Wherein the phosphorylated label moiety in Formula I above is a chromogenic moiety, it may be selected from the following: 5-bromo-4-chloro-3-indolyl phosphate, 3-indoxyl phosphate, p-nitrophenyl phosphate and derivatives thereof. The structures of these chromogenic dyes are shown as the phosphomonoesters below:

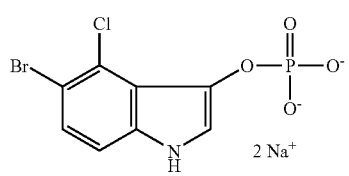

5-bromo-4-chloro-3-indolyl phospate (disodium salt)

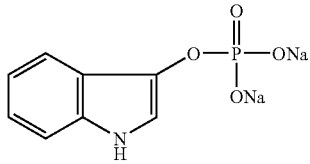

3-indolyl phospate (disodium salt)

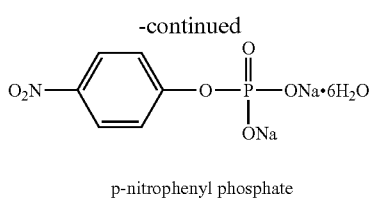

p-nitrophenyl phosphate

The moiety at the terminal-phosphate position may further be a chemiluminescent compound wherein it is desired that it is a phosphatase-activated 1,2-dioxetane compound. The 1,2-dioxetane compound may include, but is not limited to, disodium 2-chloro-5-(4-methoxyspiro[1,2-dioxetane-3, 2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3"-phosphoryloxy)phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are incorporated herein by reference.

The methods described above may further include the step of quantifying the nucleic acid sequence. In a related aspect, the detectable species may be produced in amounts substantially proportional to the amount of an amplified nucleic acid sequence. The step of quantifying the nucleic acid sequence is desired to be done by comparison of spectra produced by the detectable species with known spectra.

In one embodiment, the invention provides a method of quantifying a nucleic acid including the steps of: (a) conducting a nucleic acid polymerase reaction, the polymerase reaction including the reaction of a nucleotide which is substantially non-reactive to phosphatase in addition to at least one terminal-phosphate-labeled nucleotide, wherein the reaction results in the production of labeled polyphosphate; (b) permitting the labeled polyphosphate to react with a phosphatase to produce a detectable by-product species in an amount substantially proportional to the amount of the nucleic acid to be quantified; (c) measuring the detectable species; and (d) comparing the measurements using known standards to determine the quantity of the nucleic acid. In this embodiment of the method of quantifying a nucleic acid, the nucleic acid to be quantified may be RNA. The nucleic acid may further be a natural or synthetic oligonucleotide, chromosomal DNA, or DNA.

The invention further provides a method of quantifying a DNA sequence including the steps of: (a) conducting a DNA polymerase reaction in the presence of a terminal-phosphate-labeled nucleotide wherein the reaction results in the production of labeled polyphosphate; (b) permitting the labeled polyphosphate to react with a phosphatase to produce a detectable by-product species in amounts substantially proportional to the amount of the DNA sequence to be quantified; (c) measuring the detectable species; and (d) comparing measurements using known standards to determine the quantity of DNA. In this embodiment, the DNA sequence for quantification may include natural or synthetic oligonucleotides, or DNA isolated from cells including chromosomal DNA.

In each of these methods of quantifying a nucleic acid sequence described above, the polymerase reaction step may further include conducting the polymerase reaction in the presence of a phosphatase. As described earlier in the specification, this would permit real-time monitoring of nucleic acid polymerase activity and hence, real-time detection of a target nucleic acid sequence for quantification.

The terminal-phosphate-labeled nucleotide useful for the methods of quantifying the nucleic acid sequence provided herein may be represented by the Formula I shown above. The enzyme-activatable label becomes detectable through the enzymatic activity of phosphatase which changes the phosphate ester linkage between the label and the terminal-phosphate of a natural or modified nucleotide in such a way to produce a detectable species. The detectable species is detectable by the presence of any one of or a combination of color, fluoresence emission, chemiluminescence, mass difference or electrochemical potential. As already described above, the enzyme-activatable label may be a 1,2-dioxetane chemiluminescent compound, fluorescent dye, chromogenic dye, a mass tag or an electrochemical tag or a combination thereof. Suitable labels are the same as those described above.

As will be described in further detail in the Example Section, the present invention provides methods for determining the identity of a single nucleotide in a target nucleic acid sequence. These methods include the steps of: (a) conducting a nucleic acid polymerase reaction in the presence of at least one terminal phosphate-labeled nucleotide, which reaction results in the production of labeled polyphosphate; (b) permitting the labeled polyphosphate to react with a phosphatase to produce a detectable species; (c) detecting the presence of the detectable species; and (d) identifying the nucleoside incorporated. In desired embodiments, the terminal phosphate-labeled nucleotide includes four or more phosphates in the polyphosphate chain.

Another aspect of the invention relates to a nucleic acid detection kit including:

(a) at least one or more terminal-phosphate-labeled nucleotides according to Formula I below:

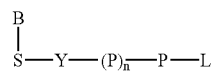

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

(b) at least one of DNA polymerase, RNA polymerase or reverse transcriptase; and (c) phosphatase.

The sugar moiety in the terminal-phosphate-labeled nucleotide included in the kit may include, but is not limited to ribosyl, 2'-deoxyribosyl, 3'-deoxyribosyl, 2',3'-dideoxyribosyl, 2',3'-didehydrodideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

The base may be, but is not limited to uracil, thymine, cytosine, 5-methylcytosine, guanine, 7-deazaguanine, hypoxanthine, 7-deazahypoxanthine, adenine, 7-deazaadenine and 2,6-diaminopurine and analogs thereof.

Furthermore, as described above, the enzyme-activatable label may be a 1,2-dioxetane chemiluminescent compound, fluorescent dye, chromogenic dye, a mass tag, an electrochemical tag or a combination thereof. Suitable compounds for conjugation at the terminal-phosphate position of the nucleotide are the same as those described above.

EXAMPLES

Example 1

Preparation of γ-(4-trifluoromethylcoumarinyl)ddGTP (γCF₃Coumarin-ddGTP)

ddGTP (200 ul of 46.4 mM solution, purity >96%) was coevaporated with anhydrous dimethylformamide (DMF, 2×0.5 ml). To this dicyclohexylcarbodiimide (DCC, 9.6 mg, 5 eq.) was added and mixture was again coevaporated with anhyd. DMF (0.5 ml). Residue was taken in anhyd. DMF (0.5 ml) and mixture was allowed to stir overnight. There was still ca 20% uncyclized triphosphate (could be from hydrolysis of cyclic trimetaphosphate on the column). To the mixture another 2 eq. of DCC was added and after stirring for 2 h, 7-hydroxy-4-trifluoromethyl coumarin (4-trifluoromethylumbelliferone, 42.7 mg, 20 eq.) and triethylamine (26 ul, 20 eq.) were added and mixture was stirred at RT. After 2 days, HPLC (0–30% acetonitrile in 0.1M triethylammonium acetate (TEAA) in 15 minutes, 30–50% acetonitrile in 5 min and 50–100% acetonitrile in 10 minutes, C18 3.9×150 mm column, flow rate 1 ml/minute) showed a new product at 9.7 min and starting cyclic triphosphate (ratio of 77 to 5 at 254 nm). Mixture was allowed to stir for another day. P-31 NMR showed gamma labeled nucleoside-triphosphate as the main component of reaction mixture. Reaction mixture was concentrated on rotary evaporator. Residue was extracted with water (5×1 ml). HPLC showed a purity of 82% at 254 nm and 81% at 335 nm. Combined aq solution was conc. on rotary evaporator and redissolved in water (1 ml). It was purified on 1 inch×300 cm C18 column using 0–30% acetonitrile in 0.1M triethylammonium bicarbonate (TEAB, pH 8.3) in 30 min and 30–50% acetonitrile in 10 min, 15 ml/min flow rate. Product peak was collected in 3 fractions. Fraction 1 was repurified using the same preparative HPLC method as above except the pH of the TEAB buffer was reduced to 6.7 by bubbling $CO_2$. Product peak was concentrated and coevaporated with MeOH (2 times) and water (1 time). Sample was dissolved in 1 ml water. HPLC showed a purity of >99% at 254 and 335 nm. UV showed a conc. of 2.2 mM assuming an extinction coeff. of 11,000 at 322 nm (reported for beta galactoside derivative of 7-hydroxy-4-trifluoromethylcoumarin, Molecular Probes Catalog). MS: M⁻=702.18 (calc 702.31), UV $\lambda_A$=253, 276 & 322 nm. The trifluorocoumarin dye attached to the gamma phosphate of ddGTP is fluorescent with an excitation maximum of 322 nm and an emission maximum of about 415 nm. Upon hydrolysis of the phosphate ester to release the free coumarin dye, the spectrum changes with excitation maximum of about 385 nm and emission maximum of about 502 nm. This change is readily detected by simple fluorescence measurements or color change. Synthesis of gamma nucleotides has been generally described by Arzumanov, A. et al. in J Biol Chem Oct. 4, 1996; 271 (40): 24389–94.

Example 2

Preparation of γ-(3-Cyanocoumarinyl)ddATP (γCNCoumarin-ddATP)

ddATP (100 μl of 89 mM solution, >96%) was coevaporated with anhydrous DMF (2×1 ml). To this DCC (9.2 mg, 5 eq.) was added and mixture was again coevaporated with anhydrous DMF (1 ml). Residue was taken in anhydrous DMF (0.5 ml) and reaction was stirred at rt. After overnight 7-hydroxy-3-cyanocoumarin (33.3 mg, 20 eq.) and TEA (25 ul, 20 eq.), were added and mixture was stirred at RT. After 1 day, a major product (55% at 254 nm) was observed 8.1 min with another minor product at 10 min (~10%). No significant change occurred after another day. Reaction mixture was concentrated on rotary evaporator and residue was extracted with 3×2 ml water and filtered. Aq solution was concentrated and purified on C-18 using 0–30% acetonitrile in 0.1M TEAB (pH 6.7) in 30 min and 30–50% acetonitrile in 10 min, flow rate 15 ml/min. Main peak was collected in 3 fractions. HPLC of the main peak (fr. 2) showed a purity of 95.6% at 254 nm and 98.1% at 335 nm. It was concentrated on rotary evaporator (at RT), coevaporated with MeOH (2×) and water (1×). Residue was dissolved in 0.5 ml water. A 5 ul sample was diluted to 1 ml for UV analysis. A346 nm=0.784. Assuming an extinction coeff. of 20,000 (reported for 7-ethoxy-3-cyanocoumarin, Molecular Probes Catalog), concentration=7.84 mM. Yield=3.92 umol, 44%. Sample was repurified on C-18 column using same method as above. Sample peak was collected in 3 fractions. Fractions 2 & 3, with >98% purity at 254 nm and >99.5% purity at 340 nm, were combined. After concentration, residue was coevaporated with MeOH (2×) and water (1×). Sample was dissolved in water (1 ml) to give a 2.77 mM solution. MS: M⁻=642.98 au (calc 643.00 au), UV $\lambda_A$=263 & 346 nm The cyanocoumarin dye attached to the gamma phosphate of ddATP is fluorescent with an excitation maximum of 346 nm and an emission maximum of about 411 nm. Upon hydrolysis of the phosphate ester to release the free coumarin dye, the spectrum changes with excitation maximum of about 408 nm and emission maximum of about 450 nm. This change is readily detected by simple fluorescence measurements or color change. Synthesis of gamma nucleotides has been generally described by Arzumanov, A, et al in J Biol Chem. Oct. 4, 1996; 271(40):24389–94.

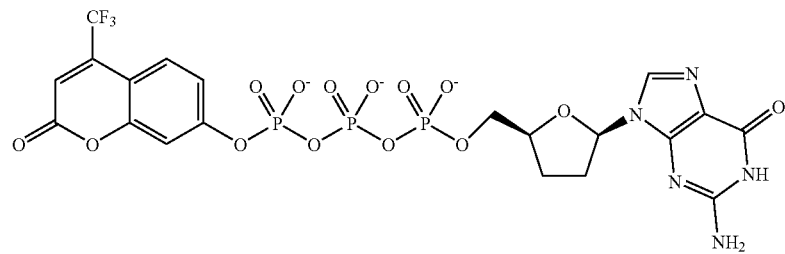

γ-(4-trifluoromethylcoumarinyl)dideoxyguanosine-5'-triphosphate (γCF₃Coumarin-ddGTP)

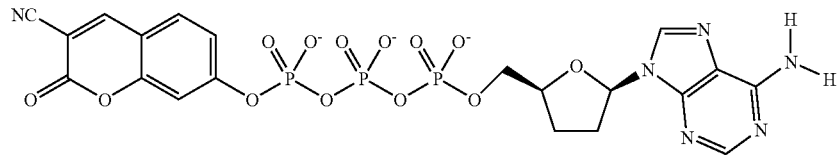

γ-(3-cyanocoumarinyl)dideoxyadenosine-5'-triphosphate (γCNCoumarin-ddATP)

Example 3

Preparation of δ-9H(1,3-dichloro-9,9-dimethylacridin-2-one-7-yl)-dideoxythymidine-5'-tetraphosphate (ddT4P-DDAO)

ddTTP (100 μl of 80 mM solution) was coevaporated with anhydrous dimethylformamide (DMF, 2×1 ml). To this dicyclohexylcarbodiimide (8.3 mg. 5 eq.) was added and the mixture was again coevaporated with anhydrous DMF (1 ml). Residue was taken in anhydrous DMF (1 ml) and reaction was stirred at room temperature overnight. HPLC showed mostly cyclized triphosphate (~82%). Reaction mixture was concentrated and residue was washed with anhydrous diethyl ether 3×. It was redissolved in anhydrous DMF and concentrated to dryness on rotavap. Residue was taken with DDAO-monophosphate, ammonium salt (5 mg, 1.5 eq.) in 200 μl anhydrous DMF and stirred at 40° C. over the weekend. HPLC showed formation of a new product with desired UV characteristics at 11.96 min. (HPLC Method: 0.30% acetonitrile in 0.1M triethylammonium acetate (pH 7) in 15 min, and 30–50% acetonitrile in 5 min, Novapak C-18 3.9×150 mm column, 1 ml/min). LCMS (ES-) also showed a major mass peak 834 for M−1 peak. Reaction mixture was concentrated and purified on Deltapak C18, 19×300 mm column using 0.1M TEAB (pH 6.7) and acetonitrile. Fraction with product was repurified by HPLC using the same method as described above. Fraction with pure product was concentrated, coevaporated with MeOH (2×) and water (1×). Residue was dissolved in water (1.2 ml) to give a 1.23 mM solution. HPCL purity as 254 nm>97.5%, at 455 nm>96%; UV $\lambda_A$=267 nm and 455 nm; MS: M−1=834.04 (calc 8.33.95).

δ-9H(1,3-dichloro-9,9-dimethylacridin-2-one-7=yl)-dideoxycytidine-5'-tetraphosphate (ddC4P-DDAO), δ-9H (1,3-dichloro-9,9-dimethylacridin-2-one-dideoxyadenosine-5'-tetraphosphate (ddA4P-DDAO) and δ-9H(1,3-dichloro-9,9-dimethylacridin-2-one-y-YL)-dideoxyguanosine-5'-tetraphosphate (ddG4P-DDAO) were synthesized and purified in a similar fashion. Analysis of these purified compounds provided the following data: ddC4P-DDAO: UV $\lambda_A$=268 nm and 454 nm; MS: M−1=819.32 (calc 818.96); ddA4P-DDAO: UV $\lambda_A$=263 nm and 457 nm; MS: M−1=843.30 (calc 842.97); ddG4P-DDAO: UV $\lambda_A$=257 nm and 457 nm; MS: M−1=859.40 (calc 858.97).

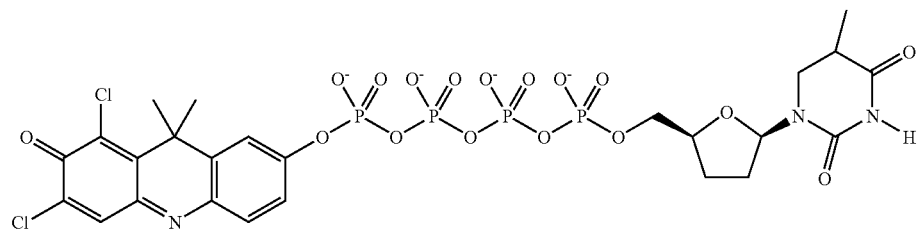

ddT4P-DDAO

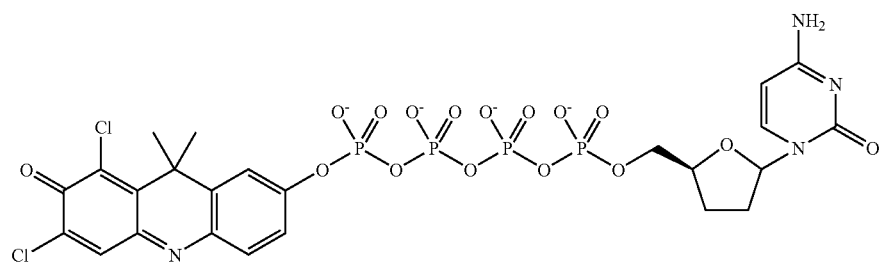

ddC4P-DDAO

-continued

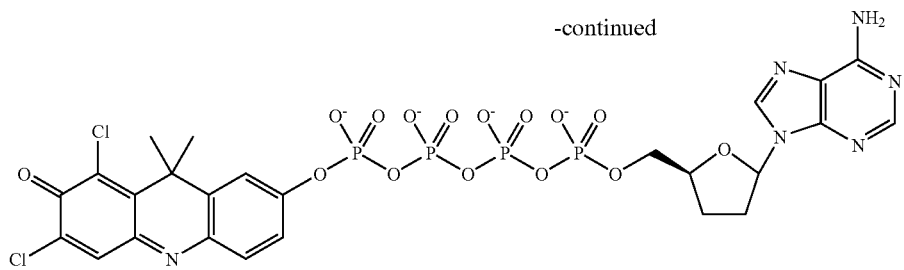

ddA4P-DDAO

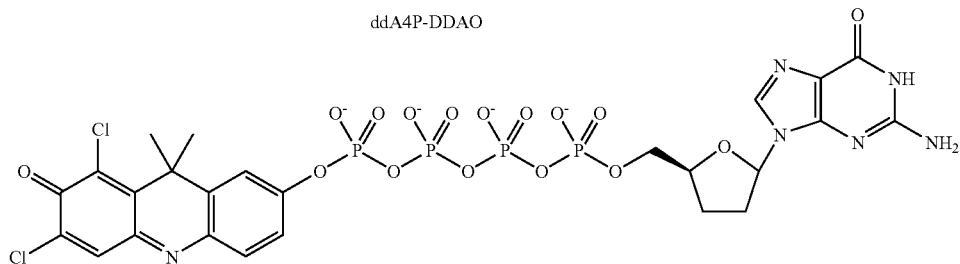

ddG4P-DDAO

Example 4

Preparation of ε-9H (1,3-dichloro-9,9-dimethylacridin-2-one-7-yl)-dideoxythymidine-5'-pentaphosphate DDAO-ddT-pentaphosphate (ddT5P-DDAO)

A. Preparation of DDAO Pyrophosphate

DDAO-phosphate diammonium salt (11.8 umol) was coevaporated with anhydrous DMF (3×0.25 ml) and was dissolved in DMF (0.5 ml). To this carbonyldiimidazole (CDI, 9.6 mg, 5 eq) was added and the mixture was stirred at room temperature overnight. Excess CDI was destroyed by addition of MeOH (5 ul) and stirring for 30 minutes. To the mixture tributylammoniumdihydrogen phosphate (10 eq., 236 ml of 0.5 M solution in DMF) was added and the mixture was stirred at room temperature for 4 days. Reaction mixture was concentrated on rotavap. Residue was purified on HiPrep 16.10 Q XL column using 0–100% B using 0.1M TEAB/acetonitrle (3:1) as buffer A and 1 M TEAB/acetonitrile (3:1) as buffer B. Main peak (HPLC purity 98%) was collected, concentrated and coevaporated with methanol (2×). Residue was dissolved in 1 ml water to give 5.9 mM solution. UV/VIS $\lambda_{max}$=456 nm.

B. Preparation of ddT5P-DDAO ddTTP (100 ul of 47.5 mM solution in water) was coevaporated with anhydrous DMF (2×1 ml). To this DCC (5 eq., 4.9 mg) was added and mixture was coevaporated with DMF (1×1 ml). Residue was taken in anhydrous DMF (0.5 ml) and stirred at room temperature for 3 hours. To this 1.03 eq of DDAO pyrophosphate, separately coevaporated with anhydrous DMF (2×1 ml) was added as a DMF solution. Mixture was concentrated to dryness and then taken in 200 ul anhydrous DMF. Mixture was heated at 38° C. for 2 days. Reaction mixture was concentrated, diluted with water, filtered and purified on HiTrap 5 ml ion exchange column using 0–100% A-B using a two step gradient. Solvent A=0.1M TEAB/acetonitrile (3:1) and solvent B=1M TEAB/acetonitrile (3:1). Fraction 12×13 which contained majority of product were combined, concentrated and coevaporated with methanol (2×). Residue was repurified on Xterra RP C-18 30–100 mm column using 0.30% acetonitrile in 0.1M TEAB in 5 column and 30–50% acetonitrile in 2 column volumes, flow rate 10 ml/min. Fraction containing pure product was concentrated and coevaporated with methanol (2×) and water (1×). HPLC purity at 455 nm>99%. UV/VIS=268 nm and 455 nm. MS: M−1=914.03 (calc 913.93).

The DDAO dye attached to the gamma phosphate of these polyphosphates is fluorescent with an excitation maximum of 455 nm and an emission maximum of about 608 nm. Upon hydrolysis of the phosphate ester to release the free dye, the spectrum changes with excitation maximum of about 645 nm and emission maximum of about 659 nm. The change is readily detected by simple fluorescence measurements or color change.

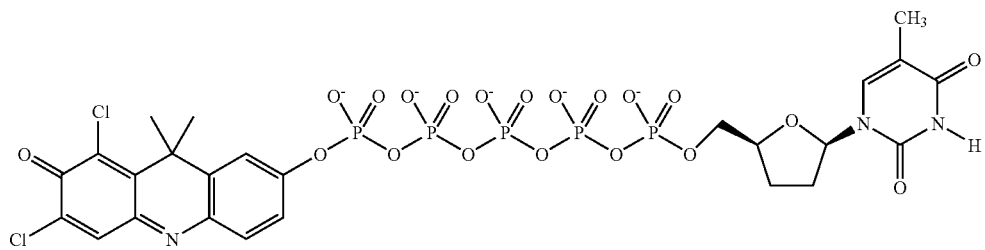

dd-T5P-DDAO

It is noted that similar nucleotide compounds with dyes or other detectable moieties attached to the terminal phosphate could also be made using similar methods to those described in Examples 1–4 above. These include ribonucleotides, deoxyribonucleotides, nucleoside-tetraphosphates, nucleotides with any of the naturally-occurring bases (adenine, guanine, cytosine, thymine, hypoxanthine and uracil) as well as modified bases or modified sugars.

Examples 5 and 6 below demonstrate that dideoxynucleotides having a dye derivative attached to the terminal phosphate may be effectively incorporated as substrates into a growing nucleic acid chain by a nucleic acid polymerase in a template-directed process for detection of a nucleic acid.

Example 5

Nucleic Acid Sequence Detection Using Polymerase Incorporation of Gamma Phosphate-labeled ddGTP Reactions were assembled at room temperature (23° C.) using the dideoxynucleotide of Example (1). Reactions contained primer template combinations having a single oligonucleotide primer (represented by SEQ ID NO: 1) annealed to one of two different oligonucleotide templates with either a dC or a dT as the next template nucleotide adjacent the 3' terminus of the primer, corresponding to SEQ ID NO: 2 and SEQ ID NO: 3, respectively.

Referring now to FIG. 1, for template 1 (SEQ ID NO: 2) in the present example, DNA polymerase would be expected to extend the primer with labeled ddGTP. Similarly, for template 2 (SEQ ID NO: 3) in FIG. 1, DNA polymerase would be expected to extend the primer with ddATP, but not with labeled ddGTP.

Reaction conditions: A 70 µl reaction containing 25 mM Tris, pH 8.0, 5% glycerol 5 mM $MgCl_2$, 0.5 mM beta-mercaptoethanol, 0.01% tween-20, 0.25 units shrimp alkaline phosphatase, 100 nM primer annealed to template (the next template nucleotide is either dCMP or dTMP, as indicated), and 2 µM ddGTP-$CF_3$-Coumarin was assembled in a quartz fluorescence ultra-microcuvet in a LS-55 Luminescence Spectrometer (Perkin Elmer), operated in time drive mode. Excitation and emission wavelengths are 390 nm and 500 nm respectively. Slit widths were 5 nm for excitation slits, 15 nm for emission slits. The reaction was initiated by the addition of 0.35 µl (11 units) of a cloned DNA polymerase I genetically engineered to eliminate 3'-5' exonuclease activity, 5'-3' exonuclease activity and discrimination against dideoxynucleotides and 0.25 mM $MnCl_2$.

As shown in FIG. 1, for reactions containing the gamma labeled ddGTP, dye emission was detected only with Primer: Template 1, where the next nucleotide in the template was a dC. Cleavage of the pyrophosphate product of phosphoryl transfer by shrimp alkaline phosphatase leads to a detectable change in the $CF_3$-coumarin label which allows for the detection of the nucleic acid. No detectable dye emission was obtained with Primer: Template 2.

Example 6

Nucleic Acid Sequence Detection Using Polymerase Incorporation of Gamma Phosphate-labeled ddATP Reactions were assembled at room temperature (23° C.) using the dideoxynucleotide of Example (2). Reactions contained primer: template combinations having a single oligonucleotide primer (SEQ ID NO: 1) annealed to one of two different oligonucleotide templates with either a dC or a dT as the template nucleotide, adjacent to the 3' terminus of the primer, corresponding to SEQ ID NO: 2 and SEQ ID NO: 3, respectively.

Figure 2:
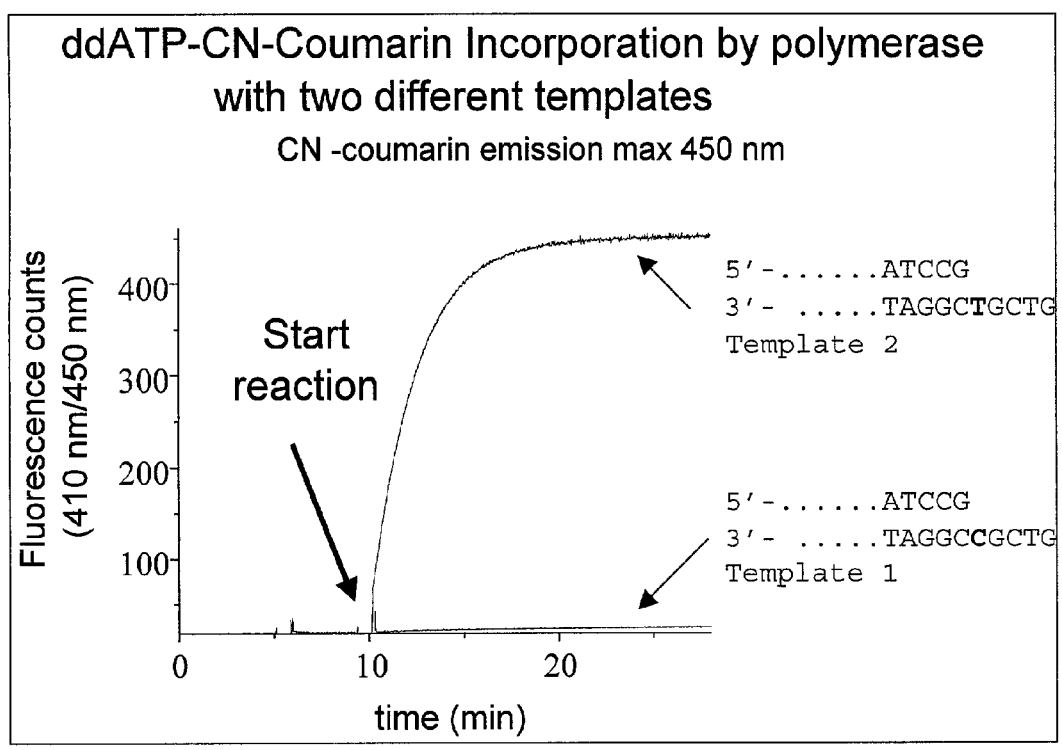
FIG. 2 is a graph showing fluorescence obtained by polymerase utilization of a gamma-phosphate-labeled ddATP in a template-directed process in the presence of phosphatase.

Referring now to FIG. 2, for template 2 (SEQ ID NO: 3) in the present example, DNA polymerase would be expected to extend the primer with labeled ddATP. Similarly, for template 1 (SEQ ID NO: 3) in FIG. 2, DNA polymerase would be expected to extend the primer with ddGTP, but not with labeled ddATP.

Reaction conditions: A 70 µl reaction containing 25 mM Tris, pH 8.0, 5% glycerol 5 mM $MgCl_2$, 0.5 mM beta-mercaptoethanol, 0.01% tween-20, 0.25 units shrimp alkaline phosphatase, 100 nM primer annealed to template, and 2 µM ddATP-CN-Coumarin was assembled in a quartz fluorescence ultra-microcuvet in a LS-55 Luminescence Spectrometer (Perkin Elmer), operated in time drive mode. Excitation and emission wavelengths are 410 nm and 450 nm respectively. Slit widths were 5 nm for excitation slits, 15 nm for emission slits. The reaction was initiated by the addition of 0.35 µl (11 units) of a cloned DNA polymerase I genetically engineered to eliminate 3'-5' exonuclease activity, 5'-3' exonuclease activity and discrimination against dideoxynucleotides and 0.25 mM $MnCl_2$.

As shown in FIG. 2, for reactions containing the gamma labeled ddATP, dye emission was detected only for Primer: Template 2, where the next nucleotide in the template was a dT. Cleavage of the pyrophosphate product of phosphoryl transfer by shrimp alkaline phosphatase produces a detectable change in the CN-coumarin label that allows one to detect the nucleic acid. No detectable dye emission was obtained with Primer: Template 1.

What is claimed is:

1. A method of detecting the presence of a nucleic acid sequence comprising the steps of:
   a) conducting a nucleic acid polymerase reaction, said reaction comprising the reaction of at least one nucleotide which is substantially non-reactive to phosphatase and at least one terminal-phosphate-labeled nucleotide, which reaction results in the production of labeled polyphosphate;
   b) permitting said labeled polyphosphate to react with a phosphatase to produce a detectable species; and
   c) detecting the presence of said detectable species.

2. The method of claim 1 wherein step (a) further comprises conducting said polymerase reaction in the presence of a phosphatase.

3. The method of claim 1 wherein said nucleic acid sequence is RNA.

4. The method of claim 1 wherein step (a) further comprises conducting said polymerase reaction in the presence of two or more terminal-phosphate-labeled nucleotides with distinct labels.

5. The method of claim 4 wherein said labels are enzyme-activatable labels selected from the group consisting of chemiluminescent compounds, fluorogenic dyes, chromogenic dyes, mass tags, electrochemical tags and combinations thereof.

6. The method of claim 1 wherein said terminal-phosphate-labeled nucleotide may be represented by formula I:

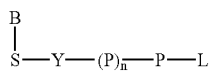

wherein P=phosphate ($PO_3$) and, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

7. The method of claim 1, wherein said terminal phosphate-labeled nucleotide comprises four or more phosphate groups in the polyphosphate chain.

8. The method of claim 1 further comprising the step of quantifying said nucleic acid sequence.

9. The method of claim 1 wherein said detectable species is produced in amounts substantially proportional to the amount of nucleic acid sequence.

10. The method of claim 1 wherein said nucleic acid sequence is a natural or synthetic oligonucleotide.

11. The method of claim 1 wherein said nucleic acid sequence is a chromosome or part of a chromosome.

12. The method of claim 1 wherein said nucleic acid sequence is DNA.

13. The method of claim 1 wherein said polymerase reaction further comprises the step of incubating a nucleic acid sequence in the presence of at least one of DNA or RNA polymerase.

14. The method of claim 1 further comprising the step of including one or more additional detection reagents in said polymerase reaction.

15. The method of claim 14 wherein said additional detection reagents are capable of a response that is detectably different from said detectable species.

16. The method of claim 14 wherein said additional detection reagent is an antibody.

17. The method of claim 6 wherein said enzyme-activatable label is selected from the group consisting of chemiluminescent compounds, fluorogenic dyes, chromogenic dyes, mass tags, electrochemical tags and combinations thereof.

18. The method of claim 1 wherein said detectable species is detectable by a property selected from the group consisting of color, fluorescence emission, chemiluminescence, mass change, reduction/oxidation potential and combinations thereof.

19. The method of claim 6 wherein said phosphorylated label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorutin phosphate, 4-triiuoromethylumbelliferylphosphate, umbelliferyl phosphate, 3-cyanoumbelliferyl phosphate, 9,9-dimethylacirdin-2-one-7-yl phosphate and 6,8-difluoro-4-methylumbelliferyl phosphate.

20. The method of claim 6 wherein said phosphorylated label is a chromogenic moiety selected from the group consisting of 5-bromo-4-chloro-3-indolyl phosphate, 3-indoxyl phosphate, p-nitrophenyl phosphate and derivatives thereof.

21. The method of claim 6 wherein said chemiluminescent compound is a phosphatase-activated 1,2-dioxetane compound.

22. The method of claim 21 wherein said 1,2 dioxetane compound is selected from the group consisting of 2-chloro-5-(4-meloxyspiro[1,2-dioxetane-3,2-(5-chloro-)tricycle[3,3,1-1$^{3,7}$]-decan]-1-yl)-1phenyl phosphate, chloroadamant-2'-ylidenemethoxyphenoxyphosphorylated dioxetane and 3-(2'-spiroadamrtre)-4-methoxy-4-(3''-phosphovloxy)phenyl-1,2-dioxetane.

23. The method of claim 6 wherein said sugar moiety is selected from the group consisting ribosyl, 2'-deoxyribosyl, 3'-deoxyribosyl, 2', 3'-dideoxyribosyl, 2', 3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, carbocyclic, acyclic and other modified sugars.

24. The method of claim 6 wherein said base is selected from the group consisting of uracil, thymine, cytosine, guanine, 7-deazaguanine, hypoxantinine, 7-deazahypoxanthine, adenine, 7-deazaadenine and 2,6-diaminopurine.

25. The method of claim 1 further comprising the step of quantifying said nucleic acid sequence by comparison of spectra produced by said detectable species with known spectra.

26. A method of detecting the presence of a DNA sequence comprising the steps of:
a) conducting a DNA polymerase reaction in the presence of a terminal-phosphate-labeled nucleotide, which reaction results in the production of a labeled polyphosphate;
b) permitting said labeled polyphosphate to react with a phosphatase to produce a detectable species; and
c) detecting the presence of said detectable species.

27. The method of claim 26 wherein step (a) further comprises conducting said polymerase reaction in the presence of a phosphatase.

28. The method of claim 26 wherein step (a) further comprises conducting said polymerase reaction in the presence of two or more terminal-phosphate-labeled nucleotides with distinct labels.

29. The method of claim 28 wherein said labels are enzyme-activatable labels selected from the group consisting of chemiluminescent compounds, fluorogenic dyes, chromogenic dyes, mass tags, electrochemical tags and combinations thereof.

30. The method of claim 26 wherein said terminal-phosphate-labeled nucleotide may be represented by formula I:

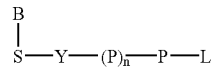

wherein P=phosphate (PO$_3$) and, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

31. The method of claim 26, wherein said terminal phosphate-labeled nucleotide comprises four or more phosphate groups in the polyphosphate chain.

32. The method of claim 26 further comprising the step of quantifying said DNA sequence.

33. The method of claim 26 wherein said detectable species is produced in amounts substantially proportional to the amount of sequence.

34. The method of claim 26 wherein said DNA sequence is a natural or synthetic oligonucleotide.

35. The method of claim 26 wherein said DNA sequence is a chromosome or part of a chromosome.

36. The method of claim 26 wherein said polymerase reaction further comprises the step of incubating a DNA sequence in the presence of a DNA polymerase.

37. The method of claim 26 further comprising the step of including one or more additional detection reagents in said polymerase reaction.

38. The method of claim 37 wherein said additional detection reagents are capable of a response that is detectably different from said detectable species.

39. The method of claim 37 wherein said additional detection reagent is an antibody.

40. The method of claim 30 wherein said enzyme-activatable label is selected from the group consisting of chemiluminescent compounds, fluorogenic dyes, chromogenic dyes, mass tags, electrochemical tags and combinations thereof.

41. The method of claim 26 wherein said detectable species is detectable by a property selected from the group consisting of color, fluorescence emission, chemiluminescence, mass change, reduction/oxidation potential and combinations thereof.

42. The method of claim 30 wherein said phosphorylated label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorutin phosphate, 4-triiuoromethylumbelliferylphosphate, umbelliferyl phosphate, 3-cyanoumbelliferyl phosphate, 9,9-dimethylacirdin-2-one-7-yl phosphate and 6,8-difluoro-4-methylumbelliferyl phosphate.

43. The method of claim 30 wherein said phosphorylated label is a chromogenic moiety selected from the group consisting of 5-bromo-4-chloro-3-indolyl phosphate, 3-indoxyl phosphate and p-nitrophenyl phosphate.

44. The method of claim 30 wherein said chemiluminescent compound is a phosphatase-activated 1,2-dioxetane compound.

45. The method of claim 44 wherein said 1,2 dioxetane compound is selected from the group consisting of 2-chloro-5-(4-meloxyspiro[1,2-dioxetane-3,2-(5-chloro-)tricycle[3,3,1-1$^{3,7}$]-decan]-1-yl)-1-phenyl phosphate, chloroadamant-2'-ylidenemethoxyphenoxyphosphorylated dioxetane and 3-(2'-spiroadamrtre)-4-methoxy-4-(3"-phosphovloxy)phenyl-1,2-dioxetane.

46. The method of claim 30 wherein said sugar moiety is selected from the group consisting of ribosyl, 2'-deoxyribosyl, 3'-deoxyribosyl, 2',3'-dideoxyribosyl, 2', 3'-didehydrodideoxy-ribosyl, 2'-alkoxyribosyl, 2'-azidoribosyl, 2'-aminoribosyl, 2'-fluororibosyl, 2'-mercaptoriboxyl, 2'-alkylthioribosyl, carbocyclic, acyclic and other modified sugars.

47. The method of claim 30 wherein said base is selected from the group consisting of uracil, thymine, cytosine, guanine, 7-deazaguanine, hypoxantinine, 7-deazahypoxanthine, adenine, 7-deazaadenine and 2,6-diaminopurine.

48. The method of claim 26 further comprising the step of quantifying said DNA sequence by comparison of spectra produced by said detectable species with known spectra.

49. A method of quantifying a nucleic acid comprising the steps of:
    (a) conducting a nucleic acid polymerase reaction, said reaction comprising the reaction of nucleotide which is substantially non-reactive to phosphatase and at least one terminal-phosphate-labeled nucleotide; said reaction resulting in production of labeled polyphosphate;
    (b) permitting said labeled polyphosphate to react with a phosphatase to produce a detectable by-product species in amount substantially proportional to the amount of said nucleic acid;
    (c) measuring said detectable species; and
    (d) comparing said measurements using known standards to determine the quantity of nucleic acid.

50. The method of claim 49 wherein step (a) further comprises conducting said polymerase reaction in the presence of a phosphatase.

51. The method of claim 49 wherein step (a) further comprises conducting said polymerase reaction in the presence of two or more terminal-phosphate-labeled nucleotides with distinct labels.

52. The method of claim 51 wherein said labels are enzyme-activatable labels selected from the group consisting of chemiluminescent compounds, fluorogenic dyes, chromogenic dyes, mass tags, electrochemical tags and combinations thereof.

53. The method of claim 49 wherein said terminal-phosphate-labeled nucleotide may be represented by formula I:

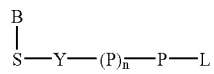

wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

54. The method of claim 53, wherein said terminal phosphate-labeled nucleotide comprises four or more phosphoryl groups in the phosphate chain.

55. The method of claim 53 wherein said phosphatase changes said phosphate ester linkage to produce said detectable species.

56. The method of claim 53 wherein said sugar moiety is selected from the group consisting of ribosyl, 2'-deoxyribosyl, 3'-deoxyribosyl, 2',3'-dideoxyribosyl, 2', 3'-didehydrodideoxy-ribosyl, 2'-alkoxyribosyl, 2'-azidoribosyl, 2'-aminoribosyl, 2'-fluororibosyl, 2'-mercaptoriboxyl, 2'-alkylthioribosyl, carbocyclic, acyclic and other modified sugars.

57. The method of claim 53 wherein said base is selected from the group consisting of uracil, thymine, cytosine, guanine, 7-deazaguanine, hypoxantinine, 7-deazahypoxanthine, adenine, 7-deazaadenine and 2,6-diaminopurine.

58. The method of claim 53 wherein said enzyme-activatable label is selected from the group consisting of chemiluminescent compounds, fluorogenic dyes, chromogenic dyes, mass tags, electrochemical tags and combinations thereof.

59. The method of claim 53 wherein detectable species is detectable by a property selected from the group consisting of color, fluorescence emission, chemiluminescence, mass change, reduction/oxidation potential and combinations thereof.

60. A method of quantifying a DNA sequence comprising the steps of:
    (a) conducting a DNA polymerase reaction in the presence of a terminal-phosphate-labeled nucleotide, said reaction resulting in production of labeled polyphosphate;
    (b) permitting said labeled polyphosphate to react with a phosphatase to produce a detectable by-product species in amounts substantially proportioned to the amount of said DNA sequence;
    (c) measuring said detectable species; and
    (d) comparing said measurements using known standards to determine the quantity of DNA.

61. The method of claim 60 wherein step (a) further comprises conducting said polymerase reaction in the presence of a phosphatase.

62. The method of claim 60 wherein step (a) further comprises conducting said polymerase reaction in the presence of two or more terminal-phosphate-labeled nucleotides with distinct labels.

63. The method of claim 62 wherein said labels are enzyme-activatable labels selected from the group consisting of chemiluminescent compounds, fluorogenic dyes, chromogenic dyes, mass tags, electrochemical tags and combinations thereof.

64. The method of claim 60 wherein said terminal-phosphate-labeled nucleotide may be represented by formula I:

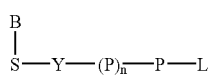

wherein P=phosphate (PO$_3$) and, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P—L is a phosphorylated label which preferably becomes independently detectable when the phosphate is removed.

65. The method of claim 64, wherein said terminal phosphate-labeled nucleotide comprises four or more phosphoryl groups in the phosphate chain.

66. The method of claim 64 wherein said phosphatase changes said phosphate ester linkage to produce said detectable species.

67. The method of claim 64 wherein said sugar moiety is selected from the group consisting of ribosyl, 2'-deoxyribosyl, 3'-deoxyribosyl, 2', 3'-didehydrodideoxyribosyl, 2',3'-dideoxyribosyl, 2'-alkoxyribosyl, 2'-azidoribosyl, 2'-aminoribosyl, 2'-fluororibosyl, 2'mercaptoriboxyl, 2'-alkylthioribosyl, carbocyclic, acyclic and other modified sugars.

68. The method of claim 64 wherein said base is selected from the group consisting of uracil, thymine, cytosine, guanine, 7-deazaguanine, hypoxantinine, 7-deazahypoxanthine, adenine, 7-deazaadenine and 2,6-diaminopurine.

69. The method of claim 64 wherein said enzyme-activatable label is selected from the group consisting of chemiluminescent compounds, fluorogenic dyes, chromogenic dyes, mass tags, electrochemical tags and combinations thereof.

70. The method of claim 60 wherein detectable species is detectable by a property selected from the group consisting of color, fluorescence emission, chemiluminescence, mass change, oxidation/reduction potential and combinations thereof.

71. A method of detecting the presence of a nucleic acid sequence comprising the steps of:
(a) conducting a nucleic acid polymerase reaction in the presence of at least one terminal-phosphate-labeled nucleotide having four or more phosphate groups in the polyphosphate chain, which reaction results in the production of a labeled polyphosphate;
(b) permitting said labeled polyphosphate to react with a phosphatase to produce a detectable species; and
(c) detecting the presence of said detectable species.

72. The method of claim 71, wherein step (a) further comprises conducting said polymerase reaction in the presence of a phosphatase.

73. The method of claim 71, further comprising the step of quantifying said nucleic acid sequence.

74. The method of claim 71, wherein step (a) further comprises conducting said polymerase reaction in the presence of two or more terminal-phosphate-labeled nucleotides with distinct labels.

* * * * *

SEQUENCE LISTING

<160> NUMBER OF SEQ ID NOS: 3

<210> SEQ ID NO 1
<211> LENGTH: 5
<212> TYPE: DNA
<213> ORGANISM: Artificial Sequence
<220> FEATURE:
<223> OTHER INFORMATION: Primer for DNA Synthesis

```
<400> SEQUENCE: 1 atccg                                                          5

<210> SEQ ID NO 2
<211> LENGTH: 10
<212> TYPE: DNA
<213> ORGANISM: Artificial Sequence
<220> FEATURE:
<223> OTHER INFORMATION: DNA Template

<400> SEQUENCE: 2
taggccgctg                                                    10

<210> SEQ ID NO 3
<211> LENGTH: 10
<212> TYPE: DNA
<213> ORGANISM: Artificial Sequence
<220> FEATURE:
<223> OTHER INFORMATION: DNA Template

<400> SEQUENCE: 3
taggctgctg                                                    10
```